United States Patent [19]

Nishikawa et al.

[11] Patent Number: 4,582,824
[45] Date of Patent: Apr. 15, 1986

[54] METHOD FOR INHIBITING ACTIVITIES OF PLATELET ACTIVATING FACTOR

[75] Inventors: Kohei Nishikawa, Kyoto; Susumu Tsushima, Suita; Hiroaki Nomura, Takatsuki, all of Japan

[73] Assignee: Takeda Chemical Industries, Ltd., Osaka, Japan

[21] Appl. No.: 614,024

[22] PCT Filed: Aug. 31, 1983

[86] PCT No.: PCT/JP83/00289
§ 371 Date: May 25, 1984
§ 102(e) Date: May 25, 1984

[30] Foreign Application Priority Data

Aug. 22, 1983 [JP] Japan .................... 58-153921

[51] Int. Cl.$^4$ ............................................ A61K 31/685
[52] U.S. Cl. ............................................ 514/77; 514/78
[58] Field of Search ............................... 514/77, 78

[56] References Cited

U.S. PATENT DOCUMENTS

| | | | |
|---|---|---|---|
| 3,752,886 | 8/1973 | Munder et al. | 514/78 |
| 4,119,714 | 10/1978 | Kny et al. | 514/78 |
| 4,372,949 | 2/1983 | Kodama et al. | 514/78 |
| 4,408,052 | 10/1983 | Hozumi et al. | 546/22 |

OTHER PUBLICATIONS

Chem. Abst., 96: 34619(f) (1982)—Hozumi et al.
Chem. Abst., 98: 192426m (1983)—Terashita et al.
Chem. Abst., 98: 210009j (1983)—Takeda Chem. Ind.
Chem. Abst., 99: 195215y (1983)—Hozumi et al.
Chem. Abst., 100: 191370m (1984)—Tsushima et al.
Chem. Abst., 102: 106288q (1985)—Valone.
Chem. Abst., 102: 6025h (1985)—Tsushima et al.
Chem. Abst., 103: 4294s (1985)—Terashita et al.

*Primary Examiner*—Douglas W. Robinson
*Attorney, Agent, or Firm*—Wegner & Bretschneider

[57] ABSTRACT

Compounds of the formula

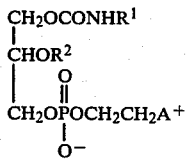

wherein $R^1$ is a $C_{10-24}$ alkyl group, $R^2$ is a $C_{1-4}$ alkyl group or a phenyl-$C_{1-3}$ alkyl group and $A^+$ is a heterocyclic group containing a quaternized nitrogen, and physiologically acceptable salts thereof have platelet activating factor inhibiting activity and are useful in the prevention and treatment of various circulatory diseases or allergic diseases.

17 Claims, No Drawings

METHOD FOR INHIBITING ACTIVITIES OF PLATELET ACTIVATING FACTOR

TECHNICAL FIELD

This invention relates to a method for inhibiting activities of platelet activating factor.

BACKGROUND ART

Platelet aggregation supposedly causes various circulatory diseases and inhibitors of platelet aggregation have occupied an important position among drugs.

The representative substances known to induce platelet aggregation are adenosine diphosphate (ADP) and metabolites of arachidonic acid such as thromboxane $A_2$ ($TXA_2$) in particular. Accordingly in the development of platelet aggregation inhibitors, the inhibition of the activity of these substances has been utilized as a primary screening indicator.

Recently, however, as a substance that displays a stronger platelet aggregation effect via a different mode of action from that of ADP and $TXA_2$, platelet activating factor (PAF) was discovered and its structure has been identified to be 1-O-alkyl-2-acetyl-sn-glyceryl-3-phosphorylcholine [Nature, 285, 193 (1980)]. It has been found that PAF has a mode of action different from that of ADP and $TXA_2$ and displays greater activity at lower concentrations. Moreover, PAF is a strong chemical transmitter of allergy and in the assay using respiratory stenosis as an indicator, this substance has been found to have the highest activity of all the known compounds [European Journal of Pharmacology, 65, 185-192 (1980)]. It is, therefore, logical to assume that if a compound inhibits the action of PAF, it could be an effective inhibitor of platelet aggregation and also be an effective drug against PAF-induced diseases such as allergies.

It is also known that PAF functions as a shock inducer [European Journal of Pharmacology, 86, 403-413 (1983)]. Shocks may arise from various causes. They may be traumatic, hemorrhagic, cardiogenic, bacterial and so on. However, the pathological condition of shock is almost the same irrespective of causes; thus, circulatory disorders such as hypotension, decreased cardiac output, etc., and such metabolic disorders as metabolic acidosis, hyperpotassemia and lactacidemia are observed. Taking bacterial shock as an example, it is most often caused by infection of gram-negative bacilli (*Escherichia coli, Pseudomonas aeruginosa,* Krebsiella, etc.) and an endotoxin which is a cell wall component of these bacteria is said to be the causative agent. Actually, a shock can be induced by injecting the endotoxin into animals. Despite progresses in antibiotic and transfusion therapies, the rate of mortality due to shock has not been reduced. Therefore, when a shock is foreseen, antibiotics are administered in combination with a drug for preventing endotoxin shocks. Among the drugs commonly used for the purpose are adrenocortical hormones such as hydrocortisone, dexamethazone, etc. However, since this type of drug is given in high doses in cases of shock, the onset of side effects presents a problem. Antiinflammatory agents such as indomethacin have also been employed but they may cause ulceration and other untoward side effects and their efficacy is not distinct, either.

The present inventors investigated the methods for inhibiting the actions of PAF associated with various circulatory diseases and allergic diseases and have completed the present invention.

DISCLOSURE OF THE INVENTION

The present invention relates to a method for inhibiting activities of platelet activating factor in mammals which comprises administering to a mammal an effective amount of a compound of the formula

wherein $R^1$ is a $C_{10-24}$ alkyl group, $R^2$ is a $C_{1-4}$ alkyl group or a phenyl-$C_{1-3}$ alkyl group and $A^+$ is a heterocyclic group containing a quaternized nitrogen atom, or a physiologically acceptable salt thereof.

Referring to the above formula (I), the $C_{10-24}$ alkyl group represented by $R^1$ may be straight or branched and includes, among others, decyl, dodecyl, tridecyl, tetradecyl, pentadecyl, hexadecyl, heptadecyl, octadecyl, nonadecyl, eicosanyl, docosanyl, farnesyl and dihydrophytyl. The group $R^1$ is preferably a $C_{14-20}$ alkyl group, more preferably a $C_{15-18}$ alkyl group and most preferably a $C_{18}$ alkyl group.

The $C_{1-4}$ alkyl group represented by $R^2$ includes, among others, methyl, ethyl, propyl, isopropyl, butyl and isobutyl, and desirably is a methyl group. The phenyl-$C_{1-3}$ alkyl group represented by $R^2$ includes, among others, benzyl and phenethyl, whose benzene ring may optionally have a substituent or substituents such as $C_{1-4}$ alkyl (e.g. methyl, ethyl, propyl, isopropyl), $C_{1-4}$ alkoxy (e.g. methoxy, ethoxy, propoxy), halogen (e.g. chloro, bromo), nitro or acetyl.

The heterocyclic group containing a quaternized nitrogen atom represented by $A^+$ includes, among others, pyridinio, oxazolio, isoxazolio, thiazolio, isothiazolio, pyridazinio, quinolinio and isoquinolinio. These heterocyclic groups may optionally have a substituent or substituents such as $C_{1-4}$ alkyl (e.g. methyl, ethyl), hydroxy, hydroxyethyl, aminoethyl, amino (imino), carbamoyl or ureido. Among the above heterocyclic groups preferred is a thiazolio group.

The compound (I) may be used in the form of a physiologically acceptable salt, which may be represented, for example, by the formula

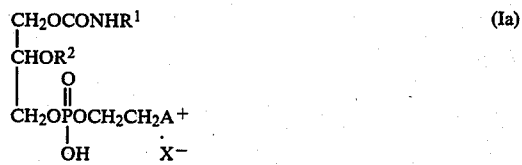

wherein $X^-$ is an anion such as chloro, bromo, iodo or tosylate ion, or by the formula

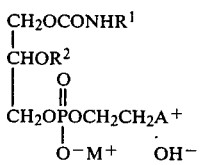

(Ib)

wherein M+ is an alkali metal (e.g. sodium, potassium) or alkaline earth metal (e.g. calcium, magnesium) ion.

Referring to the compound (I), there are two stereoisomers respectively having the R- and S-configurations with respect to the carbon atom at position 2. It should be noted that such isomers, mixtures thereof and racemate all fall within the scope of the present invention.

The glycerin derivative (I) and a salt thereof exhibits a potent platelet activating factor (PAF) inhibiting activity and, more concretely, it strongly inhibits PAF-induced platelet aggregation, shock (blood pressure drop, lethal effect, etc.) and allergy. Therefore, the compound (I) and a salt thereof can be used in the prevention and treatment of PAF-induced circulatory diseases such as thrombosis, cerebral apoplexy (e.g. cerebral hemorrhage, cerebral thrombosis), myocardial infarction, angina pectoris, thrombophlebitis, glomerulonephritis, shock (e.g. endotoxin shock, endotoxin-induced intravascular coagulation syndrome, anaphylactic shock) and the like as well as allergy-related bronchial asthma, among others.

The glycerin derivative (I) and a salt thereof are remarkably hydrophilic and lipophilic and low in toxicity. Therefore, it can be safely administered orally or otherwise either as it is or as formulated into suitable dosage forms. The dosage depends on the subject, condition, route of administration, etc. For the prevention or treatment of thrombosis in adult humans, for instance, it is advantageous to administer about 0.1 to 20 mg/kg body weight of the compound (I) per dose and once to about 3 times a day. More specifically, for the prophylaxis of thrombosis, about 0.5 to 4 mg/kg body weight and for the treatment thereof, about 4 to 10 mg/kg body weight per dose are preferably administered once to about 3 times a day.

For the prevention and treatment of shock in adult humans, for instance, by an intravenous regimen, it is advantageous to administer about 0.1 to 20 mg/kg body weight of the compound (I) per dose, preferably 1 to 10 mg/kg body weight per dose, once to about 3 times a day. The compound (I) may also be administered by drip injection in the dose of about 0.07 to 0.7 mg/kg body weight/min. per dose once to about 3 times a day. Other parenteral and oral regimens may also be used, the dosage levels being selected within the above-mentioned ranges. Moreover, in cases of very severe shock, the dosage may be increased in accordance with the severity of the condition.

Pharmaceutical compositions that can be used for the above-mentioned purposes contain an effective amount of the compound (I) or a salt thereof and a suitable amount of pharmaceutically acceptable vehicles or excipients. Such compositions are provided in dosage forms suitable for oral or parenteral administration.

Thus, compositions for oral administration are provided in solid or liquid dosage forms such as tablets (inclusive of sugar-coated, film-coated), pills, granules, powders, capsules (inclusive of soft capsules), syrups, emulsions, suspensions, etc. Such compositions are prepared by the established pharmaceutical procedures and contain vehicles or excipients commonly used by the pharmaceutical industry. Thus, for example, lactose, starch, sucrose and magnesium stearate may be mentioned.

Compositions for non-oral administration are, for example, injections, suppositories, etc. and injections include those for intravenous, subcutaneous, intracutaneous, intramuscular and drip injections. Such injections are prepared by dissolving, suspending or emulsifying the compound (I) or a salt thereof in a sterile aqueous or oleaginous liquid commonly used in the production of injectable preparations. Aqueous liquids for injection include, among others, physiological saline and isotonic solutions containing glucose and other adjuvants, and suitable solubilizers such as alcohols (e.g. ethanol), polyalcohols (e.g. propylene glycol, polyethylene glycol), nonionic surfactants [e.g. Polysorbate 80, HCO-50 (polyoxyethylene (50 mol) adduct of hydrogenated castor oil)], etc. may also be contained. The oleaginous liquids may be sesame oil, soybean oil, etc. which may be used along with such solubilizers as benzyl benzoate, benzyl alcohol, etc. The injections thus prepared are generally filled into suitable ampules. Suppositories for rectal administration are prepared by mixing the compound (I) or a salt thereof with conventional suppository bases.

These oral and non-oral pharmaceutical compositions are conveniently processed into unit dosage forms commensurate with the dose of the active ingredient. Such dosage forms include tablets, pills, capsules, injections (ampules), suppositories, etc. and desirably contain generally 5 to 500 mg of the compound (I) per dose unit, preferably 5 to 100 mg in the case of injections and 10 to 250 mg in the case of other dosage forms.

Unless an undersirable interaction is induced, these compositions may contain other active components in addition to the compound (I).

The glycerin derivative (I) can be produced, for example by the following methods:

METHOD A

The compound (I) is produced by reacting a compound of the formula

(II)

wherein Y is Cl, Br or I and the other symbols are as defined above, with a compound of the formula

(III)

wherein A is a nitrogen-containing heterocycle.

METHOD B

The compound (I) is obtained by reacting a compound of the formula $$\begin{array}{c} CH_2OH \\ | \\ CHOR^2 \\ | \quad O \\ | \quad \| \\ CH_2OPOCH_2CH_2A^+ \\ | \\ O^- \end{array} \quad (IV)$$

wherein the symbols are as defined above, with a compound of the formula $$R^1\text{—NCO} \quad (V)$$

wherein $R^1$ is as defined above, or in sequence with phosgene and a compound of the formula $$R^1\text{—NH}_2 \quad (VI)$$

METHOD C

The compound (I) is obtained by reacting a compound of the formula $$\begin{array}{c} CH_2OCONHR^1 \\ | \\ CHOR^2 \\ | \quad O \quad X \\ | \quad \| \quad / \\ CH_2OP \\ \quad \quad \backslash \\ \quad \quad \quad X \end{array} \quad (VII)$$

wherein X is Cl or Br and the other symbols are as defined above, with a compound of the formula $$HOCH_2CH_2A^+ \cdot X^- \quad (VIII)$$

wherein $X^-$ is an anion such as halide ion, $OH^-$, $CO_3^{--}$ or sulfate ion, and the other symbol is as defined above.

Referring to the above method A, the compound (III), which is used for the reaction, i.e. quaternization, is pyridine, thiazole, isothiazole, oxazole, pyridazine, quinoline or isoquinoline, for instance. Such heterocycles further may have a substituent or substituents such as mentioned above with respect to $A^+$. The reaction is carried out at room temperature or with heating (e.g. at 35°–200° C.) in the presence or absence of a sovlent using the base represented by formula (III) in an equivalent amount or in large excess (the excess serving as the solvent) as compared with the compound (II). The solvent is, for example, methanol, toluene, benzene, ether, dioxane or tetrahydrofuran.

Referring to method B, the reaction, namely conversion to carbamate ester, is accomplished by bringing 1 to 10 equivalents of (V) into contact with (IV) in the presence of a solvent such as chloroform, dichloromethane, toluene or pyridine. The reaction temperature is preferably about 0°–150° C. The reaction of (IV) with phosgene is carried out in the presence of a solvent such as toluene, benzene or chloroform at a temperature of about −20° to room temperature, and the reaction mixture, with or without removal of the excess phosgene dissolved therein, is subjected to reaction with (VI) with ice cooling or at room temperature.

The reaction in method C is accomplished by bringing (VII) into contact with (VIII) in an amount of 1 to about 1.5 moles per mole of (VII) at a temperature of 0°–100° C. in the presence of a solvent (e.g. chloroform, dichloromethane, pyridine, toluene, dioxane).

In each of the production methods mentioned above, the progress of the reaction can be followed by thin layer chromatography and accordingly the reaction conditions can adequately be selected based on the results of such chromatography.

The purification of the compounds produced by the above-mentioned methods is adequately conducted by a conventional procedure e.g. extraction with solvent, recrystallization and chromatography.

The starting compounds for the above methods A, B and C can be produced, for example by the scheme shown below or modifications thereof.

$$\begin{array}{c} CH_2OH \\ | \\ CHOR^2 \quad \xrightarrow{R^1NCO} \\ | \\ CH_2OH \end{array}$$

$$\begin{array}{c} CH_2OCONHR^1 \\ | \\ CHOR^2 \\ | \\ CH_2OH \end{array} \xrightarrow[\text{(2) }H_2O]{\text{(1)} \begin{array}{c} X \quad O \\ \backslash \| \\ P\text{—OCH}_2CH_2Y \\ / \\ X \end{array}} (II)$$

wherein the symbols are as defined above.

BEST MODE FOR CARRING OUT THE INVENTION

Production Example 1

3-(N-Octadecylcarbamoyloxy)-2-methoxypropyl 2-pyridinioethyl phosphate (1) In 20 ml of pyridine, 9.7 g of n-octadecyl isocyanate and 3.5 g of β-methylglycerolether are stirred together at room temperature overnight. The reaction mixture is poured into a mixture of 300 ml of ether and 50 ml of water and neutralized with concentrated hydrochloric acid. The ether layer is separated, washed with water, dried and concentrated to dryness. The residue is purified by silica gel chromatography [eluent: chloroform-ether (1:1)] to give 8.2 g of 3-(N-octadecylcarbamoyloxy)-2-methoxy-1-propanol as colorless crystals.

IR (infrared absorption spectrum) $\nu_{max}^{Nujol}$ cm$^{-1}$: 3340, 1687.

M.p.: 55°–56° C.

Mass spectrum (m/e): 401(M+), 370 (M—OCH$_3$)

(2) A mixture of 6.0 g of 3-(N-octadecylcarbamoyloxy)-2-methoxy-1-propanol and 4.0 g of 2-bromoethyl phosphorodichloridate are refluxed in 30 ml of carbon tetrachloride for 18 hours. After cooling, the solvent is distilled off under reduced pressure, and 50 ml of water is added. The mixture is refluxed for an hour, cooled and extracted with ether. The extract is dried with mirabilite. The solvent is then distilled off to give 7.1 g of an intermediate (the bromide compound). This intermediate (1.6 g) is dissolved in 16 ml of pyridine and the solution is warmed at 60° C. overnight. The pyridine is distilled off under reduced pressure, and 2 g of silver carbonate and 50 ml of methanol are added to the residue. The mixture is refluxed for 2 hours. The insoluble matter is filtered off and the filtrate is concentrated to dryness. The residue is purified by silica gel chromatography (eluent: chloroform-methanol-water (65:25:4), followed by reprecipitation from chloroform-acetone to give 393 mg of the captioned compound.

TLC (thin layer chromatography): Rf=0.2 [chloroform-methanol-water (65:25:4)].

Ir (KBr) cm$^{-1}$: 3340, 1698, 1540, 1470, 1255, 1075, 1050.

NMR (60 MHz, CDCl$_3$) δ: 0.7–1.8 (35H), 3.44 (3H, S, OCH$_3$), 2.9–4.8 (9H, m), 5.20 (2H, broad, CH$_2$N$^+$), 6.16 (1H, broad, CONH), 8.0~8.8 (3H, m, pyridinio), 9.58 (2H, m, pyridinio).

Elemental analysis for C$_{30}$H$_{55}$N$_2$O$_7$P.0.5H$_2$O: Calcd. C, 60.48; H, 9.48; N, 4.70; P, 5.20. Found: C, 60.20; H, 9.28; N, 4.77; P, 5.30.

Production Example 2

3-(N-Octadecylcarbamoyloxy)-2-methoxypropyl 2-thiazolioethyl phosphate

In 250 ml of benzene are dissolved 20.1 g of 3-(N-octadecylcarbamoyloxy)-2-methoxy-1-propanol and 14.5 g of 2-bromoethyl phosphorodichloridate and, with ice-cooling, 4.74 g of pyridine is added dropwise. After completion of addition, the mixture is stirred at room temperature for 6 hours. The solvent is then distilled off under reduced pressure and 200 ml of water is added to the residue. The mixture is refluxed for an hour, cooled and extracted with ether to give 29 g of an intermediate. This intermediate is dissolved in a mixture of 20 g of thiazole and 25 ml of toluene, and the solution is warmed at 60° C. for 3 days. The solvent is then distilled off. The residue is dissolved in 500 ml of methanol and 20 g of silver carbonate is added. The mixture is stirred at room temperature for 1.5 hours. The insoluble matter is filtered off and the filtrate is concentrated. The residue is purified by silica gel chromatography [eluent: chloroform-methanol-water (65:25:4)] to give 5.1 g of the captioned compound.

TLC: Rf=0.2 [chloroform-methanol-water (65:25:4)]

IR (KBr) cm$^{-1}$: 3400, 2920, 2851, 1701, 1558, 1246, 1065.

NMR (60 MHz, CDCl$_3$) δ: 0.7–1.8 (35H), 3.46 (3H, S, OMe), 2.9–4.8 (9H, m), 5.08 (2H, broad), 6.30 (1H, broad, CONH), 8.55, 8.88, 10.93 (thiazolio).

Elemental analysis for C$_{28}$H$_{53}$N$_2$O$_7$PS.1.5H$_2$O: Calcd. C, 54.26; H, 9.11; N, 4.52; P, 5.00. Found: C, 54.30; H, 8.90; N, 4.71; P, 5.03.

Production Example 3

3-(N-Decylcarbamoyloxy)-2-methoxypropyl 2-thiazolioethyl phosphate (1) In 220 ml of toluene is dissolved 25 g of n-undecanoic acid, and 51.6 g of diphenylphosphorylazide and 28.3 ml of triethylamine are added. The mixture is stirred at room temperature for 3.5 hours, concentrated to 70 ml and refluxed for 1.5 hours. After cooling, 58.3 g of β-methylglycerolether and 155 ml of pyridine are added and the mixture is stirred at room temperature overnight and concentrated to dryness. The residue is dissolved in chloroform and the solution is washed with water, dried and concentrated. The residue is subjected to chromatography with silica gel to give 20.7 g (53%) of 3-(N-decylcarbamoyloxy)-2-methoxy-1-propanol.

IR (film) cm$^{-1}$: 3340, 2920, 2850, 1700, 1255, 1065, 955, 748.

(2) In 2.1 ml of benzene are dissolved 289.4 mg (1.0 mmole) of 3-(N-decylcarbamoyloxy)-2-methoxy-1-propanol and 362.8 mg (1.5 mmole) of 2-bromoethyl phosphoryl-dichloridate, and 118.7 mg (1.5 mmole) of pyridine is added. The mixture is stirred at room temperature for 5 hours and concentrated to dryness under reduced pressure. To the residue is added 4 ml of water and the mixture is heated at 90° C. for an hour. After cooling, 10 ml of chloroform is added and the mixture is stirred vigorously. The organic layer is separated and the aqueous layer is discarded. The organic layer is concentrated to dryness under reduced pressure and 1 ml of thiazole is added to the residue. The mixture is stirred at 50° C. for 3 days and concentrated to dryness under reduced pressure. To the residue are added 5 ml of methanol and 220 mg of silver carbonate. The mixture is stirred at room temperature for an hour and the insoluble matter is filtered off. The mother liquor is concentrated to dryness under reduced pressure. The residue is purified by chromatography using a silica gel coloumn (8 g), elution being carried out with chloroform-methanol-water (65:25:4) to give 147 mg (yield: 32%) of the captioned compound as colorless powder.

Ir (film) cm$^{-1}$: 3320, 3080, 2930, 2850, 1700, 1545, 1460, 1240, 1090, 1060, 950.

NMR (60 MHz, CDCl$_3$) δ: 0.93 (3H), 1.23 (16H), 3.13 (2H), 3.38 (3H), 3.70~4.67 (7H), 4.96 (2H) 6.17 (1H), 8.33 (1H), 8.67 (1H), 10.70 (1H)

TLC: Chloroform-methanol-water (65:25:4) Rf=0.21 (1 spot).

Production Example 4

3-(N-octadecylcarbamoyloxy)-2-methoxypropyl 2-(4-methyl-5-hydroxyethyl)thiazolioethyl phosphate 3-(N-Octadecylcarbamoyloxy)-2-methoxypropyl 2-bromoethyl phosphate (294 mg) (0.5 mmole) obtained in Production Example 1 and 286.4 mg (2.0 mmoles) of 4-methyl-5-hydroxyethylthiazole are dissolved in 0.5 ml of toluene. The solution is heated at 75° C. for 3 days and concentrated to dryness under reduced pressure. The residue is purified by chromatography using a silica gel column (8 g), elution being carried out with chloroform-methanol-water (65:25:4), to give 85 mg (yield: 26.2%) of a colorless powder.

IR (film) cm$^{-1}$: 3300, 2920, 2850, 1700, 1540, 1460, 1230, 1090, 1060, 1055, 930, 850.

NMR (60 MHz, CDCl$_3$) δ: 0.90 (3H), 1.28 (32H), 2.57 (3H), 3.08 (6H), 3.43 (3H), 3.83 (6H), 4.10 (2H), 4.33 (1H), 4.77 (1H), 5.78 (1H), 10.57 (1H).

TLC: Chloroform-methanol-water (65:25:4) Rf=0.33 (1 spot).

UV (Ultraviolet absorption spectrum): λ$_{max}$ CH$_3$OH 222 mμ, 262 mμ.

Production Example 5

3-(N-Octadecylcarbamoyloxy)-2-methoxypropyl 2-isoquinolinioethyl phosphate

The bromide compound [3-(N-octadecylcarbamoyloxy)-2-methoxypropyl 2-bromoethyl phosphate, 294 mg (0.5 mmole)] obtained in Production Example 1 and 258.3 mg (2.0 mmoles) of isoquinoline are dissolved in 0.5 ml of toluene. The solution is heated at 75° C. for 3 days and concentrated to dryness under reduced pressure. The residue is purified by silica gel (8 g) column chromatography, elution being carried out with chloroform-methanol water (65:24:4) to give 140 mg (Yield: 44%) of a colorless powder.

IR (film) cm$^{-1}$: 3320, 2920, 2850, 1700, 1640, 1530, 1460, 1240, 1095, 1060, 930, 820.

NMR (60 MHz, CDCl$_3$) δ: 0.88 (3H), 1.27 (35H), 3.13 (2H), 3.32 (3H), 3.3~3.8 (2H), 3.93 (1H), 4.07 (8H), 4.63 (1H), 5.30 (1H), 6.00 (1H), 8.00 (3H), 8.50 (1H), 8.57 (1H), 9.10 (1H), 10.70 (1H).

TLC: Chloroform-methanol-water (65:25:4) Rf=0.47 (1 spot).

UV: λ$_{max}$CH$_3$OH 233 mμ, 279 mμ, 340 mμ.

Production Example 6

3-(N-Octadecylcarbamoyloxy)-2-benzyloxypropyl 2-thiazolioethyl phosphate (1) A mixture of 27 g of 1,3-benzylideneglycerol, 45 g of benzyl chloride, 300 mg of tetraethylammonium iodide, 60 ml of 50% NaOH and 240 ml of benzene is refluxed for 40 hours. The benzene layer is separated and 60 ml of 50% NaOH and 300 mg of tetraethylammonium iodide are added. The mixture is further refluxed for 20 hours. The benzene layer is separated, washed with water and concentrated. The residue is purified by silica gel chromatography (eluent: benzene) to give 36 g (yield: 89%) of 1,3-benzylideneglycerol β-benzyl ether. M.p. 73°-75° C.

(2) The ether compound (33 g) obtained in the above manner is dissolved in a mixture of 35 ml of water and 140 ml of acetic acid, and the solution is refluxed in a nitrogen gas stream for an hour. The solvent is then distilled off under reduced pressure and the residue is purified by silica gel chromatography (eluent: ether) to give 19.6 g (yield: 88%) of β-benzylglycerol.

NMR (CDCl$_3$) δ: 3.14 (2H, OH), 3.3~3.9 (5H), 4.60 (2H, PhCH$_2$—), 7.34 (5H, PhCH$_2$—).

(3) In 20 ml of pyridine is dissolved 3.64 g of β-benzylglycerol and 5.9 g of octadecyl isocyanate is added. The mixture is stirred at room temperature overnight. The pyridine is then distilled off and diluted hydrochloric acid and chloroform are added to the residue. The chloroform layer is separated, dried and concentrated. The residue is purified by silica gel chromatography [eluent: chloroform-ether (10:1)]. Recrystallization of a main product from n-hexane gives 4.1 g of 3-(N-octadecylcarbamoyloxy)-2-benzyloxy-1-propanol. M.p. 52°-54° C.

(4) In 50 ml of benzene are dissolved 3.1 g of 3-(N-octadecylcarbamoyloxy)-2-benzyloxy-1-propanol and 2.9 g of 2-bromoethyl phosphorodichloridate, and 0.96 g of pyridine is added dropwise with ice-cooling. The mixture is stirred at room temperature for 1.5 hours. The benzene is then distilled off. To the residue is added 50 ml of water and the mixture is refluxed for 45 minutes. After cooling, it was extracted with chloroform and concentrated to dryness to give 5.3 g of a white powder (the bromide compound). This compound (3.0 g) is dissolved in 6 ml of thiazole and the solution is warmed at 60° C. for 3 days. The solvent is distilled off, followed by addition of 40 ml of methanol and 3.1 g silver carbonate. The mixture is stirred at room temperature for an hour. The insoluble matter is filtered off and the filtrate is concentrated to dryness. The residue is purified by silica gel chromatography [eluent: chloroform-methanol-water (65:25:4)] to give 811 mg of the captioned compound.

IR (KBr) cm$^{-1}$: 3340, 2920, 2850, 1695, 1462, 1230, 1055.

NMR (60 MHz, CDCl$_3$) δ: 0.7-1.8 (35H), 2.9~4.9 (11H, m), 4.62 (2H, s, —CH$_2$Ph), 6.0 (1H, broad, CONH), 7.30 (5H, s, Ph), 8.21, 8.44 and 10.73 (3H, thiazolio).

Elemental analysis for: C$_{34}$H$_{57}$N$_2$O$_7$SP.2H$_2$O: Calcd. C, 57.93; H, 8.72; N, 3.97; P, 4.39. Found: C, 58.00; H, 8.91; N, 3.97; P, 4.22.

Production Example 7

3-(N-Octadecylcarbamoyloxy)-2-benzyloxypropyl 2-pyridinioethyl phosphate

In 12 ml of pyridine is dissolved 2.3 g of the intermediate (bromide compound) obtained in Production Example 6, and the solution is warmed at 60° C. for 16 hours. The pyridine is distilled off under reduced pressure. To the residue are added 2.3 g of silver carbonate and 30 ml of methanol, and the mixture is refluxed for an hour. The insoluble matter is filtered off and the filtrate is concentrated to dryness. The residue is purified by silica gel chromatography [eluent: chloroform-methanol-water (65:25:4)] to give 770 mg of the captioned compound.

TLC: Rf=0.35 [chloroform-methanol-water (65:25:4)].

Infrared absorption spectrum (KBr) cm$^{-1}$: 2910, 2840, 1695, 1245, 1070.

NMR (60 MHz, CDCl$_3$) δ: 0.8-1.8 (35H), 2.7~5.1 (13H), 6.10 (1H, broad, CONH), 7.27 (5H, s, Ph), 7.66~8.47 (3H, broad, pyridinio), 9.10 (2H, broad, pyridinio).

Elemental analysis for: C$_{36}$H$_{59}$N$_2$O$_7$.1.5H$_2$O: Calcd. C, 62.68; H, 9.06; N, 4.06. Found: C, 62.80; H, 8.80; N, 4.47.

Production Example 8

3-(N-Docosylcarbamoyloxy)-2-methoxypropyl 2-thiazolioethyl phosphate (1) In a mixture of 70 ml of dry toluene and 3.6 ml of triethylamine is dissolved 7.08 g (2×10$^{-2}$ moles) of tricosanoic acid, and 6.6 g (2.4×10$^{-1}$ moles) of diphenylphosphorylazide is added dropwise at room temperature. The mixture is stirred at room temperature for 3 hours, concentrated to one-third of its original volume, and refluxed for 1.5 hours. After cooling, 30 ml of pyridine and 7.84 g (7.4×10$^{-2}$ moles) of 2-methoxy-1,3-propyleneglycol. The mixture is stirred at room temperature overnight and concentrated to dryness under reduced pressure. Water is added to the residue, followed by extraction with chloroform. The chloroform layer is washed with water and dried over sodium sulfate. The solvent is then distilled off and the residue is purified by silica gel (100 g) column chromatography. The chloroform eluate fraction is concentrated to dryness to give 4.3 g (47%) of 3-(N-docosylcarbamoyloxy)-2-methoxy-1-propanol as a colorless powder.

IR (KBr) cm$^{-1}$: 3350 (NH, OH), 2920 (CH), 2850 (CH), 1685 (—NHCOO—), 1530 (—NHCOO—).

(2) In 20 ml of benzene are dissolved 2.74 g of 3-(N-docosylcarbamoyloxy)-2-methoxy-1-propanol and 1.89 g of 2-bromoethyl phosphorodichloridate, and 0.62 g of pyridine is added dropwise. The mixture is stirred at room temperature for 2.5 hours. The benzene is then distilled off and water is added. The mixture is reluxed for 1.5 hours, cooled and extracted with chloroform. The extract is concentrated to dryness and 6.4 ml of thiazole is added to the residue. The mixture is warmed at 60° C. for 77.5 hours and concentrated to dryness. To the residue are added 80 ml of methanol and 2.15 g of silver carbonate and the mixture is refluxed for an hour. After filtration when hot, the filtrate is concentrated to dryness to give a crude product, which is purified by silica gel chromatography [eluent: chloroform-methanol-water (65:25:4)] and recrystallized from chloroform-acetone to give 0.41 g (10.5%) of the captioned compound.

IR (KBr) cm$^{-1}$: 2820, 2850, 1700, 1245, 1065.

Elemental analysis for: $C_{32}H_{61}N_2O_7PS.2H_2O$: Calcd. C, 56.12; H, 9.57; N, 4.09; P, 4.52; S, 4.68. Found: C, 56.14; H, 9.47; N, 4.07; P, 4.68; S, 4.24.

Production Example 9

3-(N-Tetradecylcarbamoyloxy)-2-methoxypropyl 2-thiazolioethyl phosphate (1) In 200 ml of toluene is dissolved 20 g of pentadecanoic acid, and 27.3 g of diphenylphosphorylazide and 14.9 ml of triethylamine are added. The mixture is stirred at room temperature for 5 hours, concentrated under reduced pressure, and refluxed for an hour. After cooling, 32.8 g of β-methylglycerolether and 124 ml of dry pyridine are added. The mixture is stirred at room temperature overnight and concentrated to dryness. The residue is dissolved in chloroform, washed with water, dried and purified by silica gel chromatography (eluent: chloroform) to give 9.43 g (33%) of 2-methoxy-3-(N-tetradecylcarbamoyloxy)-1-propanol.

IR $\nu_{max}^{KBr}$ (cm$^{-1}$): 1695.

(2) In 73 ml of benzene are dissolved 5.18 g of 2-methoxy-3-(N-tetradecylcarbamoyloxy)-1-propanol and 5.44 g of 2-bromoethyl phosphorodichloridate, and 1.78 g of pyridine is added dropwise. The mixture is stirred at room temperature for 2 hours. The benzene is then distilled off and water is added. The mixture is refluxed for 1.5 hours. After cooling, extraction with chloroform is carried out and the extract is concentrated to dryness. To the residue is added 7 ml of thiazole, and the mixture is warmed at 60° C. for 60 hours then concentrated to dryness. To the residue are added 90 ml of methanol and 8 g of silver carbonate. The mixture is refluxed for an hour and filtered when hot and the filtrate is concentrated to dryness. The residue is purified by silica gel chromatography and recrystallized from chloroform-acetone to give 0.4 g (5%) of the captioned compound.

IR (KBr) cm$^{-1}$: 2920, 2850, 1700, 1230, 1050.

Elemental analysis for: $C_{24}H_{45}N_2O_7PS.2H_2O$: Calcd. C, 50.33; H, 8.27; N, 4.89; P, 5.41; S, 5.60. Found: C, 50.35; H, 8.20; N, 4.76; P, 5.38; S, 4.84.

Production Example 10

2-Methoxy-3-pentadecylcarbamoyloxypropyl 2-thiazolioethyl phosphate (1) In 50 ml of toluene is dissolved 5.13 g of n-hexadecanoic acid, and 5.5 g of diphenylphosphorylazide and 3 ml of triethylamine are added. The mixture is stirred for 2 hours and further refluxed for one hour. After cooling, the mixture is dissolved in 20 ml of dichloromethane and the solution is added to 20 ml of dichloromethane containing 4.2 g of 2-methylglycerin is added dropwise over a period of 30 minutes. Then, the mixture is refluxed for 2 hours, followed by addition of 200 ml of ice-water. The mixture is stirred vigorously. The dichloromethane layer is separated, dried over sodium sulfate and concentrated to dryness. The residue is subjected to chromatography on a silica gel (60 g) column [eluent: ethyl acetate-n-hexane (1:1)] to give 5.25 g (yield: 73%) of 2-methyl-3-pentadecylcarbamoylglycerin as a colorless powder.

M.p. 42.5°–43° C.

IR (KBr) cm$^{-1}$: 3350, 2920, 2850, 1690, 1530, 1465, 1280, 1260, 1245, 1230, 1150, 1130, 1080, 1055, 1040.

NMR (60 MHz, CDCl$_3$) δ: 0.88 (3H), 1.27 (26H), 2.30 (1H), 3.09 (2H), 3.46 (3H), 3.53 (2H), 3.65 (1H), 4.20 (2H), 4.83 (1H).

(2) In 18 ml of toluene are dissolved 3.23 g of 2-methyl-3-pentadecylcarbamoylglycerin and 3.70 g of 2-bromoethyl phosphorodichloridate, and 1.21 g of pyridine is added dropwise. The mixture is stirred for 3 hours and concentrated to dryness under reduced pressure. The residue is suspended in 40 ml of water and the suspension is refluxed for an hour and extracted with 40 ml of ether. The ether layer is concentrated to dryness under reduced pressure. The residue is dissolved in 5 ml of toluene solution containing 3.83 g of thiazole. The solution is stirred at 65° C. overnight, refluxed for 4 hours, and concentrated to dryness under reduced pressure. The residue is subjected to chromatography on a silica gel. (45 g) column [eluent: chloroform-methanol-water (65:25:4)] to give 1.05 g (yield: 21.2%) 2-methoxy-3-pentadecylcarbamoyloxypropyl-2-thiazolioethyl phosphate as a colorless powder.

TLC: Rf=0.20 [silica gel, chloroform-methanol-water (65:25:4)].

IR (film) cm$^{-1}$: 3350, 2920, 2850, 1700, 1550, 1465, 1240, 1095, 1060, 910.

NMR (60 MHz, CDCl$_3$) δ: 0.88 (3H), 1.22 (26H), 3.10 (2H), 3.38 (3H), 3.55 (1H), 3.73 (2H), 4.13 (6H), 4.95 (2H), 6.00 (1H), 8.33 (1H), 8.60 (1H), 10.53 (1H).

Elemental analysis for: $C_{25}H_{47}N_2O_7PS.1H_2O$: Calcd. C, 52.80; H, 8.68; N, 4.93; P, 5.45. Found: C, 52.56; H, 8.87; N, 4.93; P, 5.36.

Production Example 11

2-Methoxy-3-hexadecylcarbamoyloxypropyl 2-thiazolioethyl phosphate (1) A mixture of 5.41 g of n-heptadecanoic acid and 5.5 g of diphenylphosphorylazide is treated in accordance with the manner of Production Example 10-(1) to give 5.45 g (yield: 72.9%) of 2-methyl-3-hexadecylcarbamoylglycerin as a colorless crystalline powder.

M.p. 47.5°–48° C.

IR (KBr) cm$^{-1}$: 3350, 2920, 2850, 1690, 1530, 1465, 1280, 1260, 1245, 1230, 1150, 1130, 1080, 1055, 1040.

(2) A mixture of 3.36 g of 2-methyl-3-hexadecylcarbamoylglycerin and 3.70 g of 2-bromoethyl phosphorodichloridate is treated in accordance with the manner of Production Example 10-(2), followed by quaternization with 5 ml of toluene solution containing 3.83 g of thiazole and separation and purification in accordance with the manner of Production Example 10-(2) to give 1.35 g (yield: 26.6%) of 2-methoxy-3-hexadecylcarbamoyloxypropyl 2-thiazolioethyl phosphate as a colorless powder.

TLC: Rf=0.20 [silica gel, chloroform-methanol-water (65:25:4)].

IR (film) cm$^{-1}$: 3350, 2920, 2850, 1700, 1550, 1465, 1240, 1095, 1060, 910.

Elemental analysis for: $C_{26}H_{49}N_2O_7PS.H_2O$: Calcd. C, 53.59; H, 8.82; N, 4.81; P, 5.32. Found: C, 53.69; H, 9.08; N, 4.90; P, 5.35.

Production Example 12

2-methoxy-3-heptadecylcarbamoyloxypropyl 2-thiazolioethyl phosphate (1) A mixture of 5.69 g of n-octadecanoic acid and 5.50 g of diphenylphosphorylazide is treated in accordance with the manner of Production Example 10-(1) to give 5.41 g (yield: (70.0%) of 2-methyl-3-heptadecylcarbamoylglycerol as a colorless crystalline powder.

M.p. 52°-52.5° C.

IR (KBr) cm$^{-1}$: 3350, 2920, 2850, 1690, 1530, 1465, 1280, 1260, 1245, 1230, 1150, 1130, 1080, 1055, 1040.

(2) A mixture of 3.49 g of 2-methyl-3-heptadecylcarbamoylglycerol and 3.70 g of 2-bromoethylphosphorodichloridate is treated in accordance with the manner of Production Example 10-(2) to give 0.812 g (yield: 15.6%) of 2-methoxy-3-heptadecylcarbamoyloxypropyl 2-thiazolioethyl phosphate as a colorless powder.

TLC: Rf=0.20 [silica gel, chloroform-methanol-water (65:25:4)].

IR (film) cm$^{-1}$: 3350, 2850, 1700, 1550, 1465, 1240, 1095, 1060, 910, 730.

Elemental analysis for: $C_{27}H_{51}N_2O_7PS \cdot 1.5H_2O$: Calcd. C, 53.54; H, 8.98; N, 4.62; P, 5.11. Found: C, 53.42; H, 9.14; N, 4.61; P, 5.22.

The compounds obtained in Production Examples 3-12 are novel compounds.

Experimental Example 1

PAF-inhibiting activity

Activity to inhibit PAF in platelet aggregation

[Method and results]

Using an injection syringe containing a 3.15% solution of citric acid (in a ratio of 1 part per 9 parts of blood) as an anticoagulant, the blood was directly collected from a male rabbit. Then, at room temperature, the blood was centrifuged at 1,000 r.p.m. for 10 minutes to harvest a platelet rich plasma (PRP). This PRP was further centrifuged at 1,400 r.p.m. for 15 minutes to give a platelet pellet. The pellet was suspended in Ca$^{++}$-free Tyrode solution (containing 0.25% of gelatin) to give a washed PRP. This washed PRP (250 μl) was stirred at 37° C. for 2 minutes, then 25 μl of a 0.2 to 0.5 mM Ca$^{++}$ solution was added, and the mixture was further stirred for 30 seconds. Then, the test compound was added to the above platelet preparation to a level of $3 \times 10^{-5}$M. After stirring the mixture for 2 minutes, $3 \times 10^{-7}$M of PAF was added. The degree of platelet aggregation was determined with a platelet aggregometer (Rika Denki). The activity of the test compound was estimated from the inhibition rate as compared with the maximum optical transmission (maximum aggregation) of control PRP by PAF.

The results are shown in Table 1.

TABLE 1

| Test Compound (Production Example No.) | Inhibition rate (%) |
| --- | --- |
| 1 | 95 |
| 2 | 100 |
| 3 | 12 |
| 4 | 33 |
| 5 | 37 |
| 6 | 79 |
| 7 | 19 |
| 8 | 24 |
| 10 | 100 |
| 11 | 100 |
| 12 | 100 |

Experimental Example 2

PAF-inhibiting activity in respiratory stenosis

Male and female Hartley strain guinea pigs weighing about 400 g were used. Under urethane anesthesia (1.5 g/kg, i.p.), each animal was immobilized in supine position and one shank of a tracheal cannula (of 4-shank type) was inserted into the airway, with two of the remaining three shanks being connected to a Harvard Apparatus rodent respirator and the remaining one shank to a bronchospasm transducer (Ugo-basile Model 7020). At an air volume of 5 to 7 ml per cycle, an air supply frequency of 70 times/min. and a lung loading pressure of 10 cm H$_2$O, the volume of overflowing air was recorded through the transducer on a rectigraph (Rectigraph-8S, Sanei Sokki K.K.). After gallamine triethodide (1 mg/kg, i.v.) treatment, 10 μg/mg of histamine 2HCl was intravenously administered to examine the response of the animal. When 0.3 μg/kg of PAF was intravenously administered to control group intravenously pretreated with physiological saline, a miximum airway stenosis was noted after 30 minutes and the amount of stenosis taking a complete stenosis as 100% was 72.8±4.3 (mean±S.D., for 6 cases). The compound of Production Example 2, when intravenously administered 2 minutes before at the dose levels of 0.3 and 1 mg/kg, suppressed the above response by PAF by 49% and 82%, respectively.

Experimental Example 3

Inhibitory activity against circulatory shock due to PAF in anesthetized dogs

[Method and Results]

Male and female mongrel dogs weighing 9 to 13 kg were used. Under pentobarital sodium (30 μg/kg, i.v.) anesthesia and supportive respiration, a thoracotomy was performed at the left fourth interspace. The origin of the left coronary circumflex and the aortic arch were released, an electromagnetic probe was attached to each, and the coronary blood flow (CoF) and cardiac output (CO) were measured. Moreover, a polyethylene cannula was inserted from the apex of the heart into the left ventricle and the left ventricular pressure (LVP) was measured by means of a pressure transducer. In addition, its first-order differential dp/dt was determined by way of a differential circuit. The mean blood pressure (MBP) was continuously recorded on an ink-writing polygraph through a pressure transducer via a cannula inserted into the right femoral artery and the heart rate (HR) was similarly recorded via a tachometer driven by mean blood pressure pulse waves. PAF and the compound of Production Example 2 were respectively dissolved in physiological saline and administered via a cannula into the left femoral vein. After 1.0 μg/kg of PAF was intravenously administered and the respective parameters recovered to normal, the compound of Production Example 2 (10 mg/kg) was intravenously administered. After 10 minutes, 1.0 μg/kg of PAF was intravenously administered to estimate the anti-PAF activity of the compound of Production Example 2. All values are in percents relative to the values prior to PAF administration. The results are shown in Table 2.

The intravenous administration of 1.0 μg/kg of PAF was immediately followed by a fall in mean blood pressure (MBP) [systolic (SBP) and diastolic (DBP) pressures fell by similar degrees], left ventricular pressure (LVP) and the maximum value of its first-order differential (max dp/dt), cardiac output (CO) and coronary blood flow (CoF), and the degree of decreases was about 50 to 70% in 1 to 2 minutes. The decrease of CO was particularly remarkable. The duration of action was long and it took 60 minutes before the preadministration values were recovered. Heart rate (HR) showed only a slight decrease. These parameters were almost completely inhibited by the pretreatment with the compound of Production Example 2.

TABLE 2

The influence of PAF on cardiac hemodynamics and the anti-PAF effect of Compound (I)

|  | Influence of PAF (1.0 μg/kg, i.v.) | | | Influence of PAF (1.0 μg/kg i.v.) after pretreatment with the compound of Production Example 2 (10 mg/kg, i.v.) | | |
| --- | --- | --- | --- | --- | --- | --- |
|  | 0.5 (min) | 1 (min) | 5 (min) | 0.5 (min) | 1 (min) | 5 (min) |
| SBP | 70 ± 5 | 52 ± 5 | 59 ± 9 | 90 ± 3* | 99 ± 1*** | 102 ± 3* |
| DBP | 58 ± 3 | 47 ± 3 | 67 ± 12 | 78 ± 5* | 99 ± 1*** | 101 ± 2 |
| MBP | 62 ± 4 | 49 ± 5 | 63 ± 11 | 87 ± 7* | 99 ± 1*** | 101 ± 2* |
| LVP | 81 ± 1 | 59 ± 7 | 62 ± 6 | 92 ± 3* | 97 ± 3** | 100 ± 1** |
| Max $\frac{dp}{dt}$ | 76 ± 8 | 50 ± 3 | 54 ± 7 | 94 ± 7 | 98 ± 2*** | 102 ± 3** |
| HR | 96 ± 8 | 95 ± 8 | 89 ± 3 | 109 ± 2 | 105 ± 1 | 103 ± 3* |
| CO | 93 ± 13 | 33 ± 3 | 35 ± 7 | 107 ± 4 | 99 ± 2*** | 103 ± 5** |
| CoF | 75 ± 3 | 77 ± 3 | 56 ± 2 | 109 ± 4 | 103 ± 3** | 97 ± 3*** |

Each value is the mean ± S.D. (%) (n = 3)
*$P < 0.05$, $P < 0.01$, *$P < 0.001$
As compared with control without pretreatment with the compound of Production Example 2.

Experimental Example 4

Anti-endotoxin shock activity in rats

[Method and Results]

Male Sprague-Dawley rats weighing 500 to 600 g were used under pentobarbital sodium (50 mg/kg, i.v.) anesthesia. A cannula was inserted into the femoral artery and secured in position for measurement of blood pressure and another cannula into the femoral vein for administration of a solution of the drug. The blood pressure was measured via a pressure transducer and recorded on a polygraph. For a control group, a suspension of endotoxin (Lipopolysaccharide W. E. coli 0111: B4, Wako Pure Chemical) in physiological saline was administered into the femoral vein and the maximum hypotensive response occurring 3 to 5 minutes after administration was recorded. On the other hand, for the administration of 3-(N-n-octadecylcarbamoyloxy)-2-methoxypropyl 2-thiazolioethyl phosphate [hereinafter, compound (IA)], the compound (IA) was dissolved in physiological saline and administered into the femoral vein in a dose of 10 mg/kg. Ten (10) minutes after the administration of (IA), endotoxin was similarly administered and the maximum hypotensive response was recorded. The anti-endotoxin shock activity of the test compound was estimated from the difference in blood pressure response between the (IA) treatment group and the non-(IA) treatment group. The results are shown in Table 3. Whereas rats given endotoxin alone showed a remarkable blood pressure fall of 46 mmHg on the average, rats in the (IA) treatment group showed a pressure fall of only 15 mmHg on the average, indicating that compound (IA) has a significant anti-endotoxin shock activity.

TABLE 3

Inhibitory effect of compound (IA) on endotoxin-induced blood pressure fall

| Drug | Dosage mg/kg i.v. | No. of Cases | Before drug administration (mmHg) | Max. hypotensive response after drug administration ($-\Delta$mmHg) |
| --- | --- | --- | --- | --- |
| Endotoxin | 15 | 4 | 103 ± 5 | 46 ± 5 |
| Compound (IA) + endotoxin | 10 + 15 | 3 | 113 ± 14 | 15 ± 3** |

(1) Each value in the table denotes the mean ± standard deviation (SD).
(2) Significance test: Student's t-test **$P < 0.01$ Experimental Example 5

Preventive effect against endotoxin-induced death in mice

[Method and Results]

Male mice of ICR-Jcl strain, aged 5 weeks and with a body weight of about 30 g, were used in groups of 7 individuals. For the control group, 15 mg/kg of endotoxin was suspended in 0.1 ml/10 g of physiological saline and injected into the tail vein. For the compound (IA) treatment group, 10 mg/kg of the compound (IA) and 15 mg/kg of endotoxin were suspended in 0.1 ml/10 g of physiological saline and similarly injected into the tail vein. The mice were examined for death up to 20 hours after the treatment.

The results are shown in Table 4. Whereas all the animals given endotoxin alone died (7/7), only one death was observed in the (IA) treatment group (1/7). It was, therefore, clear that the compound (IA) has strong prophylactic activity against endotoxin shock.

TABLE 4

Preventive effect against endotoxin-induced death in mice

| Drug | Dosage mg/kg i.v. | No. of cases | No. of deaths within 20 hrs. after drug administration | |
| --- | --- | --- | --- | --- |
|  |  |  | Deaths/survivals | Mortality (%) |
| Endotoxin | 15 | 7 | 7/7 | 100 |
| Compound (IA) + endotoxin | 10 + 15 | 7 | 1/7 | 14 |

Preparation Example 1

In 1.0 l of distilled water was dissolved 10 g of 3-(N-n-octadecylcarbamoyloxy)-2-methoxypropyl 2-thiazolioethyl phosphate, and after bacterial filtration, the solution was aseptically distributed in 1 ml portions into vails and lyophilized After drying, the vials were sealed.

On the other hand, 2 l of distilled water for injection containing 100 g of xylitol or mannitol was aseptically distributed in 2 ml portions into 1000 injection ampuls which were then fusion-sealed. For administration, one vial equivalent of this powder is extemporaneously dissolved in xylitol (or mannitol) solution for injection.

Preparation Example 2

Tablets

Per tablet,
(1) 100 mg of 3-(N-n-octadecylcarbamoyloxy)-2-methoxypropyl 2-thiazolioethyl phosphate,
(2) 200 mg of lactose,
(3) 51 mg of corn starch, and
(4) 9 mg of hydroxypropylcellulose are mixed and granulated in the conventional manner. Then, 8 mg of corn starch and 2 mg of magnesium stearate are added and the mixture is tableted to give a 370 mg tablet, 9.5 mm in diameter.

Preparation Example 3

The tablet prepared in 2 above is coated with an acetone-ethanol (4:6) solution containing 14 mg of hydroxypropylmethylcellulose phthalate and 1 mg of castor oil in a concentration of 7% to give an enteric-coated tablet.

INDUSTRIAL APPLICABILITY

The method for inhibiting the activity of platelet activating factor which is provided by this invention is useful for the prevention and treatment of various diseases.

We claim:

1. A method for inhibiting activities of platelet activating factor in mammals which comprises administering to a mammal a therapeutically effective amount of a compound of the formula

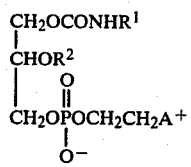

wherein $R^1$ is a $C_{10-24}$ alkyl group, $R^2$ is a $C_{1-4}$ alkyl group or a phenyl-$C_{1-3}$ alkyl group and $A^+$ is a heterocyclic group containing a quaternized nitrogen, or a physiologically acceptable salt thereof.

2. The method according to claim 1, wherein $R^1$ is a $C_{14-20}$ alkyl group.

3. The method according to claim 1, wherein $R^1$ is a $C_{15-18}$ alkyl group.

4. The method according to claim 1, wherein $R^1$ is n-octadecyl.

5. The method according to claim 1, wherein $R^2$ is a $C_{1-4}$ alkyl group.

6. The method according to claim 1, wherein $R^2$ is methyl.

7. The method according to claim 1, wherein $A^+$ is pyridinio, oxazolio, isoxazolio, thiazolio, isothiazolio, pyridazinio, quinolinio or isoquinolinio, said group being substituted or unsubstituted by $C_{1-4}$ alkyl, hydroxy, hydroxyethyl, aminoethyl, amino, imino, carbamoyl or ureido.

8. The method according to claim 1, wherein $A^+$ is pyridinio, thiazolio, (4-methyl-5-hydroxyethyl)thiazolio or isoquionolinio.

9. The method according to claim 1, wherein $A^+$ is thiazolio.

10. The method according to claim 1, wherein $R^1$ is a $C_{15-18}$ alkyl group, $R^2$ is a $C_{1-4}$ alkyl group and $A^+$ is thiazolio.

11. The method according to claim 1, wherein the compound (I) or a physiologically acceptable salt thereof is administered for the prevention or treatment of a platelet activating factor-induced circulatory disease.

12. The method according to claim 11, wherein the circulatory disease is thrombosis.

13. The method according to claim 11, wherein the circulatory disease is shock.

14. The method according to claim 13, wherein the shock is endotoxin shock.

15. The method according to claim 1, wherein the compound (I) or a physiologically acceptable salt thereof is administered for the prevention or treatment of a platelet activating factor-induced allergic disease.

16. The method according to claim 15, wherein the allergic disease is respiratory stenosis.

17. The method according to any of claim 1 and claims 11–16, wherein the compound (I) is 3-(N-n-octadecylcarbamoyloxy)-2-methoxypropyl 2-thiazolioethyl phosphate.

* * * * *